United States Patent
Lee et al.

(10) Patent No.: US 8,227,877 B2
(45) Date of Patent: Jul. 24, 2012

(54) SEMICONDUCTOR BIO-SENSORS AND METHODS OF MANUFACTURING THE SAME

(75) Inventors: Ming-Tung Lee, Taoyuan (TW); Shih-Chin Lien, Sinjhuang (TW); Chia-Huan Chang, Zhunan Township, Miaoli County (TW)

(73) Assignee: Macronix International Co., Ltd., Hsin-Chu (TW)

( * ) Notice: Subject to any disclaimer, the term of this patent is extended or adjusted under 35 U.S.C. 154(b) by 145 days.

(21) Appl. No.: 12/835,909

(22) Filed: Jul. 14, 2010

(65) Prior Publication Data

US 2012/0012900 A1 Jan. 19, 2012

(51) Int. Cl.
*H01L 27/14* (2006.01)
*H01L 23/58* (2006.01)

(52) U.S. Cl. ........ 257/414; 257/639; 257/640; 257/641; 257/644; 257/649; 257/650; 257/E27.114

(58) Field of Classification Search .................. 257/414, 257/639, 640, 641, 644, 649, E27.114
See application file for complete search history.

(56) References Cited

U.S. PATENT DOCUMENTS

| | | | | |
|---|---|---|---|---|
| 2004/0227236 A1* | 11/2004 | Sawamoto | ..................... | 257/734 |
| 2007/0085077 A1* | 4/2007 | Yu et al. | ........................... | 257/40 |
| 2009/0267164 A1* | 10/2009 | Wunnicke et al. | ............ | 257/414 |
| 2011/0248319 A1* | 10/2011 | Rothberg et al. | ............. | 257/253 |
| 2012/0015467 A1* | 1/2012 | Kim et al. | ........................ | 438/49 |

* cited by examiner

*Primary Examiner* — Ngan Ngo
(74) *Attorney, Agent, or Firm* — Alston & Bird LLP

(57) ABSTRACT

A method of manufacturing a semiconductor bio-sensor comprises providing a substrate, forming a first dielectric layer on the substrate, forming a patterned first conductive layer on the first dielectric layer, the patterned first conductive layer including a first portion and a pair of second portions, forming a second dielectric layer, a third dielectric layer and a fourth dielectric layer in sequence over the patterned first conductive layer, forming cavities into the fourth dielectric layer, forming vias through the cavities, exposing the second portions of the patterned first conductive layer, forming a patterned second conductive layer on the fourth dielectric layer, forming a passivation layer on the patterned second conductive layer, forming an opening to expose a portion of the third dielectric layer over the first portion of the patterned first conductive layer, and forming a chamber through the opening.

7 Claims, 13 Drawing Sheets

SEMICONDUCTOR BIO-SENSORS AND METHODS OF MANUFACTURING THE SAME

BACKGROUND OF THE INVENTION

The present invention generally relates to a method of manufacturing a semiconductor device and, more particularly, to a method of manufacturing a semiconductor bio-sensor.

With the growth of semiconductor industry and the progress in semiconductor process, computing, communication and consumer devices have been increasingly designed with a compact size. As well, bio-sensors are manufactured in shrinking scales that may therefore fulfill the requirements of portability and compactness. FIGS. 1A to 1C are schematic cross-sectional views illustrating a method of manufacturing a semiconductor bio-sensor in prior art. Referring to FIG. 1A, a substrate 10 may be provided. A first dielectric layer 11 which may include, for example, silicon dioxide ($SiO_2$), may then be formed on the substrate 10. The first dielectric layer 11 may serve as a pad layer.

Referring to FIG. 1B, next, a patterned conductive layer 12 which may include, for example, poly-silicon, may be formed on the first dielectric layer 11. The patterned conductive layer 12 may serve as a sensing resistor for the bio-sensor 1. A portion 12-1 of the patterned conductive layer 12 may be lightly implanted or doped with a first-type impurity, for example, an n-type impurity, which may provide the required resistance for the sensing resistor. Furthermore, second portions 12-2 of the patterned conductive layer 12 may be heavily implanted or doped with the first-type impurity to form electrical contact regions for the sensing-resistor.

Referring to FIG. 1C, a second dielectric layer 14 which may include, for example, $SiO_2$, may then be formed on the patterned conductive layer 12 and the first dielectric layer 11. The second dielectric layer 14 may serve as an insulator for the sensing-resistor of the bio-sensor 1.

With an increasing demand of integrating bio-sensors with other semiconductor devices, it is required to fabricate the bio-sensors and semiconductor devices in a complementary metal-oxide-semiconductor (CMOS) process. However, unfortunately, the thin insulator layer 14 and conductor layer 12 of the bio-sensor, if not properly protected, may be easily damaged in the CMOS process. It may therefore be desirable to have a method that is able to manufacture a semiconductor bio-sensor with other semiconductor devices in a CMOS process.

BRIEF SUMMARY OF THE INVENTION

The present invention is directed to a method for manufacturing a semiconductor bio-sensor that may be integrated with other CMOS devices on a single wafer.

Examples of the present invention may provide a method of manufacturing a semiconductor bio-sensor. The method may comprise providing a substrate, forming a first dielectric layer on the substrate, forming a patterned first conductive layer on the first dielectric layer, the patterned first conductive layer including a first portion and a pair of second portions to sandwich the first portion, forming a second dielectric layer on the patterned first conductive layer, the second dielectric layer having an etch rate greater than that of the patterned first conductive layer, forming a third dielectric layer on the second dielectric layer, forming a fourth dielectric layer on the third dielectric layer, the fourth dielectric layer having an etch rate greater than that of the thirds dielectric layer, forming cavities into the fourth dielectric layer by an isotropic etch, forming vias through the cavities by an anisotropic etch, exposing the second portions of the patterned first conductive layer, forming a patterned second conductive layer on the fourth dielectric layer, which fills the cavities and results in pads over the second portions of the patterned first conductive layer, forming a passivation layer on the patterned second conductive layer, forming an opening by an anisotropic etch, the opening exposing a portion of the third dielectric layer over the first portion of the patterned first conductive layer, and forming a chamber between the pads by an isotropic etch through the opening.

Some examples of the present invention may also provide a method of manufacturing a semiconductor bio-sensor. The method may comprise providing a substrate, forming a first dielectric layer on the substrate, forming a patterned first conductive layer on the first dielectric layer, the patterned first conductive layer including a first portion and a pair of second portions, forming a second dielectric layer, a third dielectric layer and a fourth dielectric layer in sequence over the patterned first conductive layer, forming cavities into the fourth dielectric layer, forming vias through the cavities, exposing the second portions of the patterned first conductive layer, forming a patterned second conductive layer on the fourth dielectric layer, forming a passivation layer on the patterned second conductive layer, forming an opening to expose a portion of the third dielectric layer over the first portion of the patterned first conductive layer, and forming a chamber through the opening.

Examples of the present invention may further provide a semiconductor bio-sensor. The semiconductor bio-sensor may comprise a substrate, a first dielectric layer on the substrate, a patterned first conductive layer on the first dielectric layer, the patterned first conductive layer including a first portion and a pair of second portions to sandwich the first portion, a second dielectric layer on the patterned first conductive layer, the second dielectric layer having an etch rate greater than that of the patterned first conductive layer, a third dielectric layer on the second dielectric layer, a fourth dielectric layer on the third dielectric layer, the fourth dielectric layer having an etch rate greater than that of the third dielectric layer, a pair of pads over the second portions in electrical connection with the second portions, a patterned second conductive layer on the pads, and a channel region between the pads to expose the third dielectric layer.

Additional features and advantages of the present invention will be set forth in portion in the description which follows, and in portion will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, examples are shown in the drawings. It should be understood, however, that the invention is not limited to the precise arrangements and instrumentalities shown in the examples.

In the drawings.

DETAILED DESCRIPTION OF THE INVENTION

Reference will now be made in detail to the present examples of the invention illustrated in the accompanying drawings. Wherever possible, the same reference numbers will be used throughout the drawings to refer to the same or like portions. It should be noted that the drawings are in greatly simplified form and are not to precise scale.

Figure 1A:
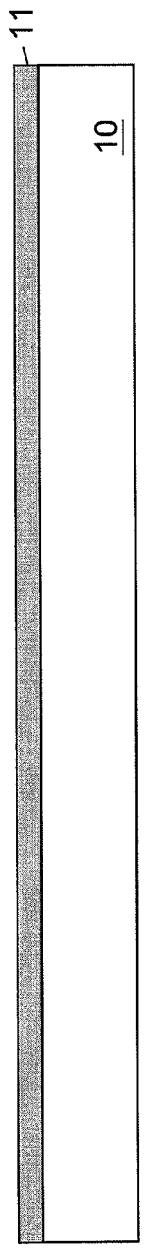
FIGS. 1A to 1C are schematic cross-sectional views illustrating a method of manufacturing a semiconductor bio-sensor in prior art.
Figure 1B:
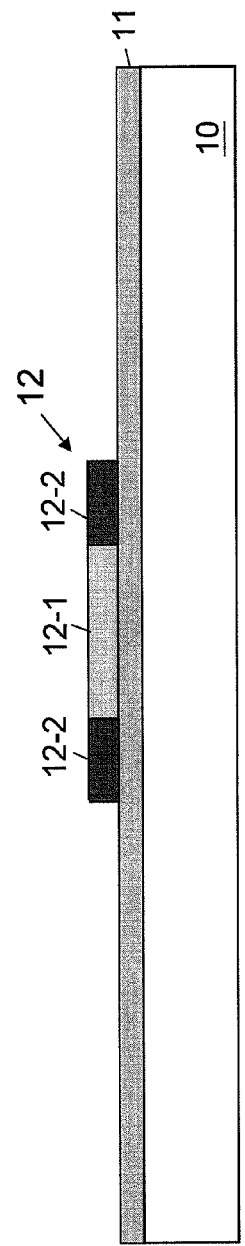
Figure 1C:
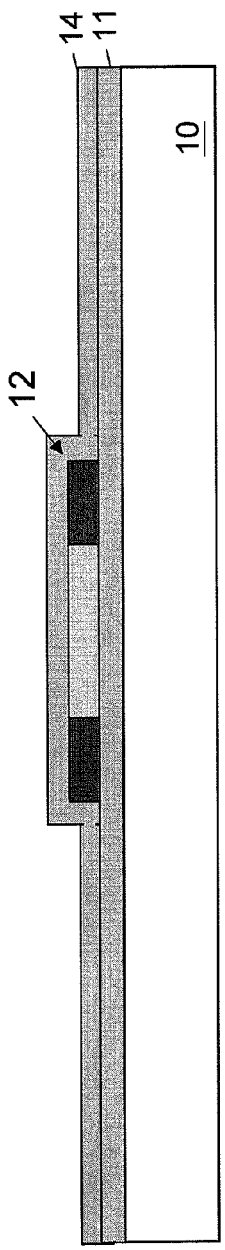
Figure 2A:
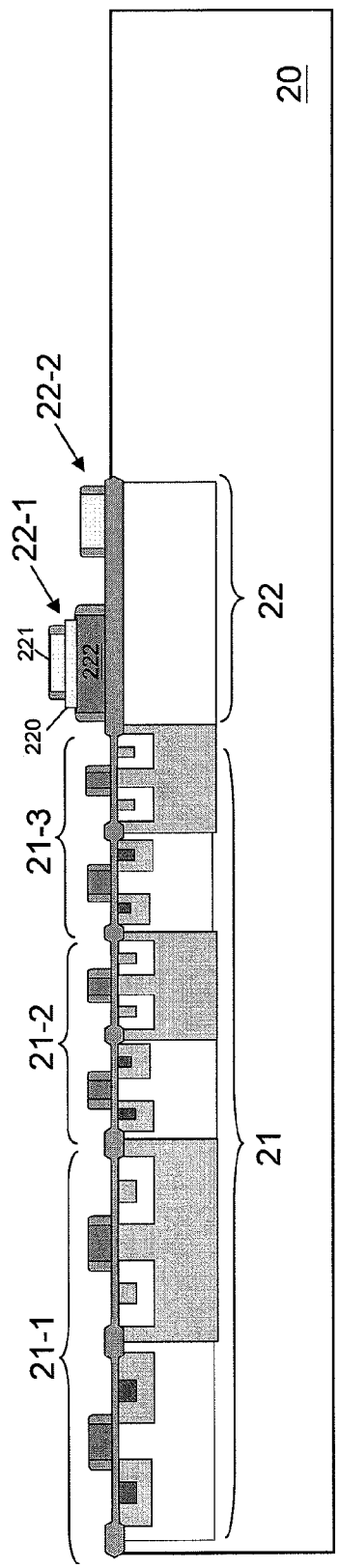
FIGS. 2A to 2M are schematic cross-sectional views illustrating a method of manufacturing a semiconductor bio-sensor in accordance with an example of the present invention.

FIGS. 2A to 2M are schematic cross-sectional views illustrating a method of manufacturing a semiconductor bio-sensor in accordance with an example of the present invention. Referring to FIG. 2A, a substrate 20 that has been doped with a first-type impurity, for example, a p-type impurity, may be provided. Next, a plurality of complementary metal oxide semiconductor (CMOS) devices 21, i.e., complementary and symmetrical pairs of first-type and second-type devices such as n-type and p-type metal oxide semiconductor field effect transistors (MOSFETs), may be formed in the substrate 20. In one example, the CMOS devices 21 may comprise a pair of first-type and second-type MOSFETs 21-1 which may operate under a relatively high operating voltage, for example, 12 Volts (V), another pair of first-type and second-type MOSFETs 21-2 which may operate under a moderate operating voltage, for example, 5V and still another pair of first-type and second-type MOSFETs 21-3 which may operate under a relatively low operating voltage, for example, 3V. Each of the MOSFETs 21-1, 21-2 and 21-3 may serve as, for example, a switch device.

Moreover, a plurality of peripheral devices 22 may be formed beside the CMOS devices 21 in the substrate 20. In one example, the peripheral devices 22 may comprise a capacitor 22-1 and a resistor 22-2. The capacitor 22-1 may include a first electrode 221, a second electrode 222 and a dielectric layer 220 between the first and second electrodes 221 and 222. The capacitor 22-1 may sense a pressure applied thereon and therefore serve as a sound sensor, for example, a microphone. The resistor 22-2 may have a tunable resistance and may serve as a thermopile sensor to detect a change in temperature. The CMOS devices 21 and the peripheral devices 22 may be formed at a first region of the substrate 20 in a CMOS process.

Figure 2B:
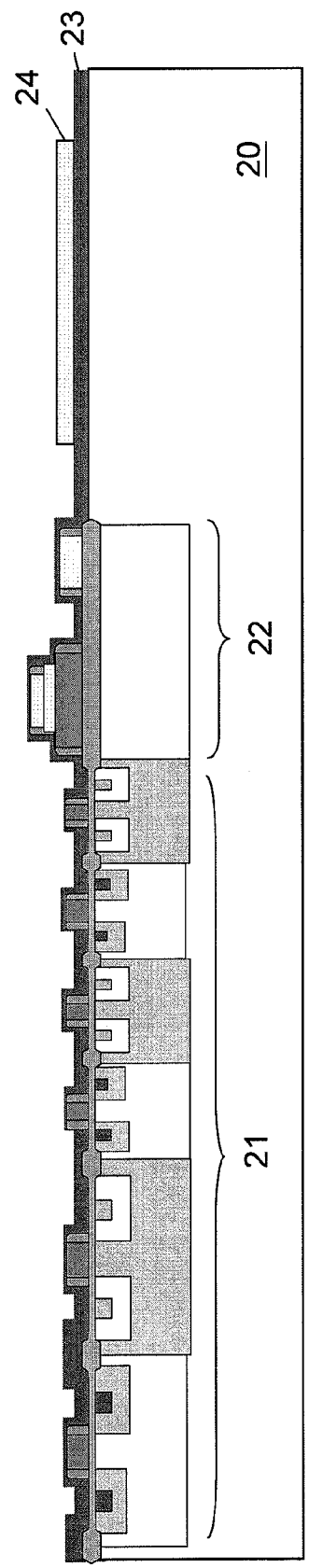

Referring to FIG. 2B, a first dielectric layer 23 may be formed on the CMOS devices 21, the peripheral devices 22 and the substrate 20 by a deposition process. In one example, the first dielectric layer 23 may include undoped silicon glass silicon dioxide (USGOX) having a thickness ranging from approximately 900 angstroms (Å) to 1100 Å. The first dielectric layer 23 may serve as a pad layer.

Next, a patterned first conductive layer 24 may be formed beside the peripheral devices 22 at a second region of the substrate 20 by a deposition process followed by a lithography process and an etching process. In one example, the patterned first conductive layer 24 may include poly-silicon having a thickness ranging from approximately 500 Å to 700 Å. In another example, the patterned first conductive layer 24 may include poly-silicon germanium (poly-SiGe). In still another example, the patterned first conductive layer 24 may include monocrystalline silicon or nanocrystal-silicon. The patterned first conductive layer 24 may serve as a sensing resistor for the bio-sensor.

Figure 2C:
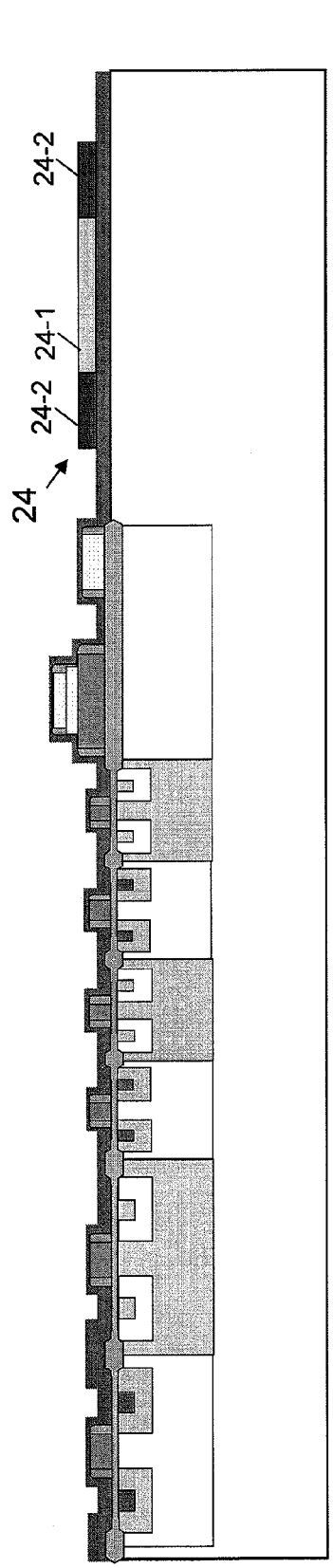

Referring to FIG. 2C, the patterned first conductive layer 24 may then be implanted with one of the first-type or the second-type impurity. Specifically, in one example, a first portion 24-1 of the patterned first conductive layer 24 may be lightly implanted with the first-type impurity having a concentration ranging from approximately $2.5 \times 10^{14}$ cm$^{-2}$ to $5 \times 10^{14}$ cm$^{-2}$. The lightly implanted portion 24-1 of the patterned first conductive layer 24 may serve as a resistive region that provides required resistance for the sensing resistor. Furthermore, a pair of second portions 24-2 of the patterned first conductive layer 24, which sandwich the first portion 24-1, may be heavily implanted with the first-type impurity having a concentration of approximately $3 \times 10^{15}$ cm$^{-2}$. The heavily implanted portions 24-2 of the patterned first conductive layer 24 may serve as electrical contact regions for the sensing resistor.

In another example, the first portion 24-1 of the patterned first conductive layer 24 may be lightly implanted with the second-type impurity, i.e., an n-type impurity, having a concentration ranging from approximately $2.5 \times 10^{14}$ cm$^{-2}$ to $5 \times 10^{14}$ cm$^{-2}$ to form a resistive region for the sensing resistor, and the second portions 24-2 of the patterned first conductive layer 24 may be heavily implanted with the second-type impurity having a concentration of approximately $3 \times 10^{15}$ cm$^{-2}$ to form electrical contact regions for the sensing resistor of the bio-sensor. Although in the present example the first portion 24-1 is implanted before the second portions 24-2, however, a person skilled in this art should understand that the sequence of implantation may be interchangeable.

Figure 2D:
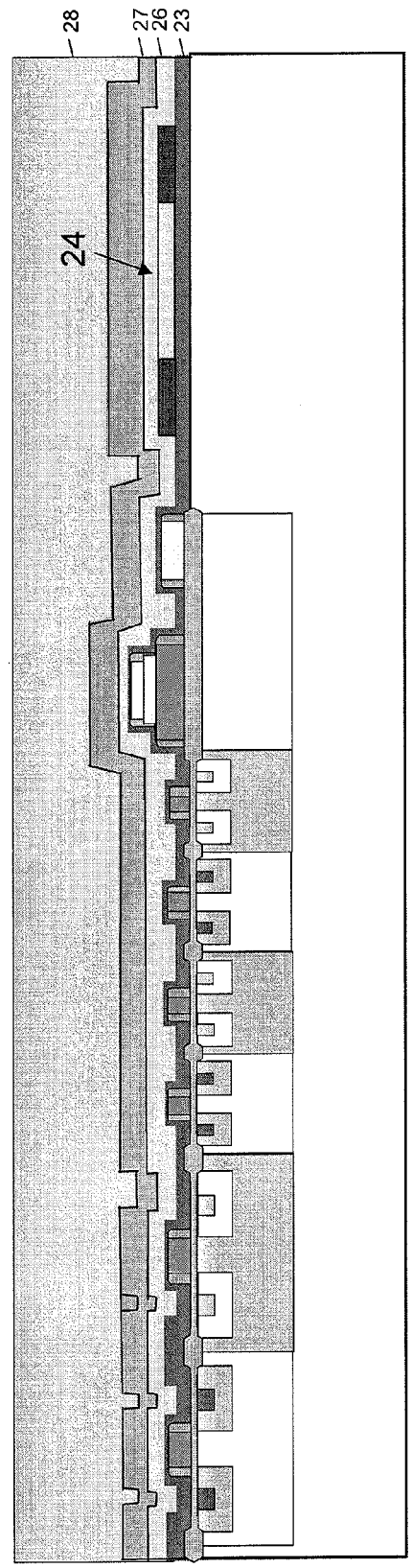

Referring to FIG. 2D, a second dielectric layer 26 may then be formed on the first dielectric layer 23, the patterned first conductive layer 24 and the substrate 20 by a deposition process. The second dielectric layer 26 may exhibit desirable adhesion with the patterned first conductive layer 24. In one example, the second dielectric layer 26 may include SiO$_2$ having a relatively thin thickness ranging from approximately 40 Å to 50 Å. In another example, the second dielectric layer 26 may include silicon oxynitride (SiON). The second dielectric layer 26 may serve as a first insulator that may provide desirable adhesiveness with the sensing resistor.

Furthermore, a third dielectric layer 27 may be formed on the second dielectric layer 26 by a deposition process. In one example, the third dielectric layer 27 may include silicon nitride (Si$_3$N$_4$) having a relatively thin thickness ranging from approximately 130 Å to 140 Å. In another example, the third dielectric layer 27 may include aluminum nitride (AlN). The third dielectric layer 27 may serve as a second insulator that may provide electrical insulation between subsequent layers formed thereon and the sensing resistor. In still another example, a third insulator (not shown) of silicon oxynitride (SiON) may optionally be formed between the first and the second insulators, i.e. the second and third dielectric layers 26 and 27.

Next, a fourth dielectric layer 28 may be formed on the third dielectric layer 27 by a deposition process followed by a planarization process such as a chemical mechanical polish (CMP) process. In one example, the fourth dielectric layer 28 may include a first sub-layer (not shown) of USGOX having a thickness ranging from approximately 900 Å to 1100 Å and a second sub-layer (not shown) of boron phosphate silicon glass (BPSG) having a thickness of approximately 7000 Å. The fourth dielectric layer 28 may serve as an inter-layer dielectric (ILD) layer.

Figure 2E:
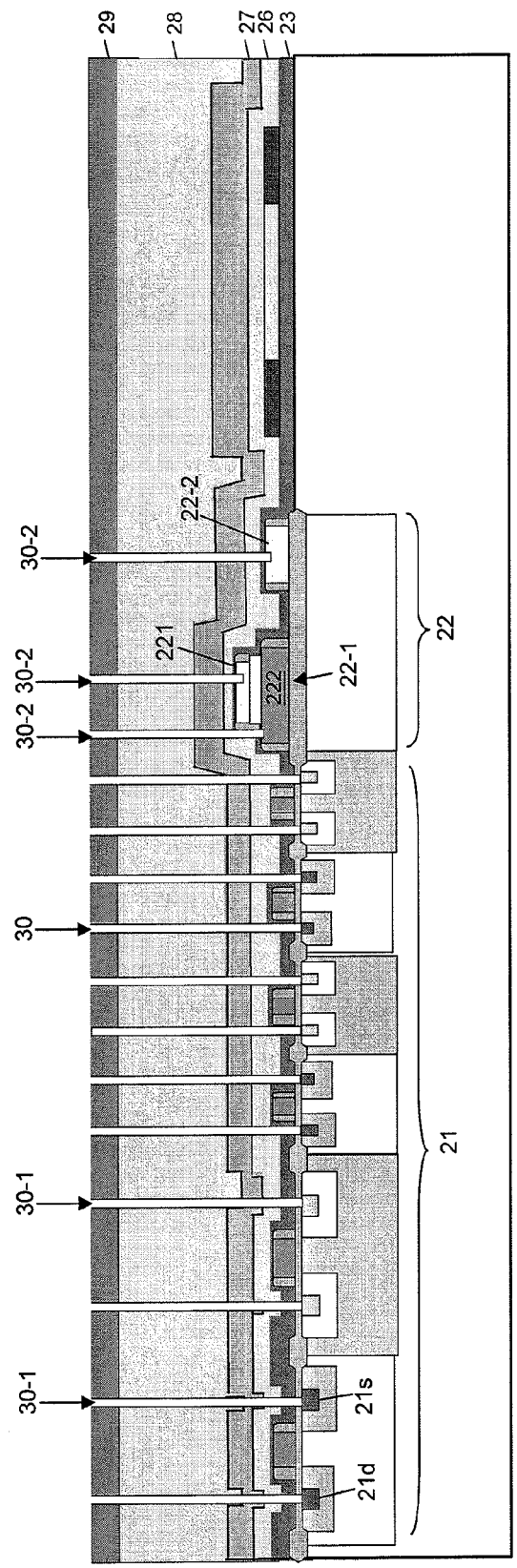

Referring to FIG. 2E, a patterned first mask layer 29 may then be formed on the fourth dielectric layer 28 by a coating process. In one example, the patterned first mask layer 29 may include photo-resist. Using the patterned first mask 29 layer as a mask, a plurality of first vias 30 may be formed through the first to the fourth dielectric layers 23, 26, 27 and 28 over the CMOS devices 21 and the peripheral devices 22 by an anisotropic etch such as a dry etching process. Specifically, some first vias 30-1 may expose the drain 21d and the source 21s regions of each of the MOSFETs 21. Furthermore, other first vias 30-2 may expose the resistor 22-2 and the first and second electrodes 221 and 222 of the capacitor 22-1.

Figure 2F:
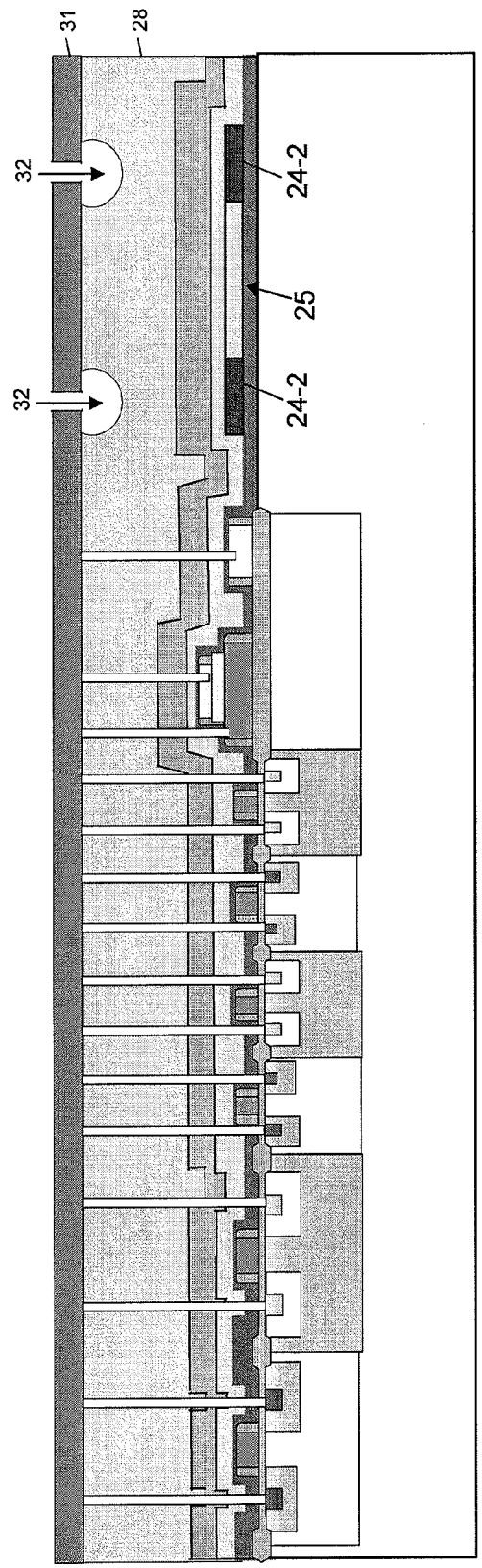

Referring to FIG. 2F, the patterned first mask layer 29 may then be stripped and a patterned second mask layer 31 may be formed on the fourth dielectric layer 28. Using the patterned second mask layer 31 as a mask, first cavities 32 may be formed into the fourth dielectric layer 28 over the electrical contact regions 24-2 of the sensing resistor by an isotropic etch such as a wet etching process.

Figure 2G:
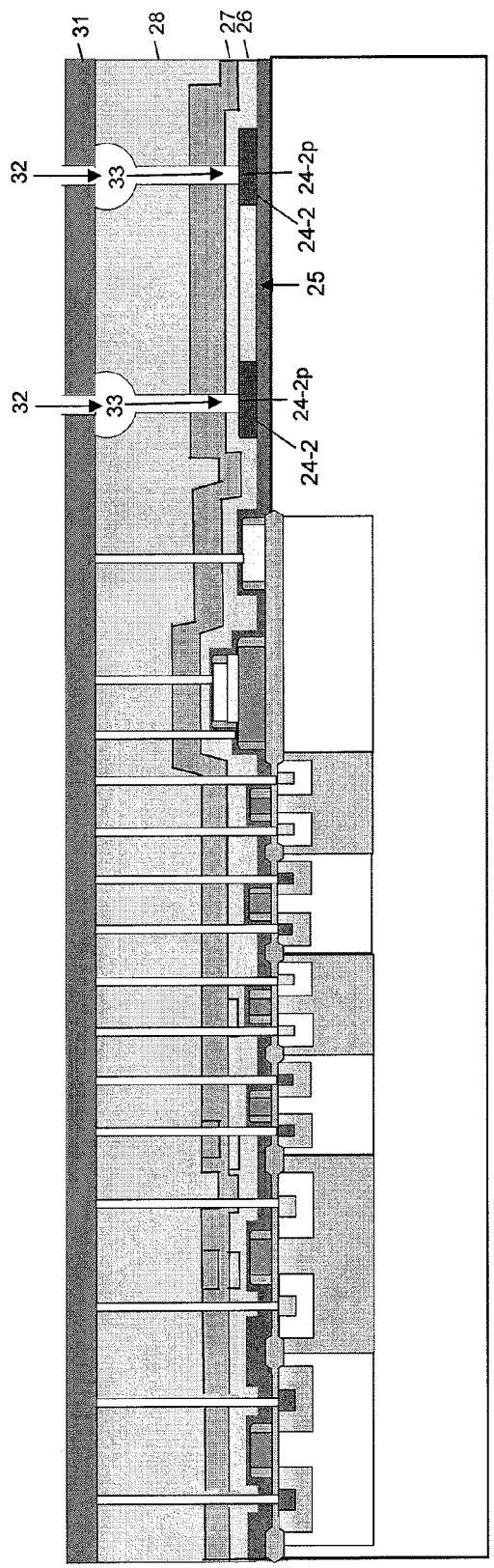

Referring to FIG. 2G, through the first cavities 32, second vias 33 may be formed through the second, the third and the fourth dielectric layers 26, 27 and 28 by an anisotropic etching process using the patterned second mask layer 31 as a mask. In one example, the anisotropic etching process may have a higher etching-selectivity for $SiO_2$ than for poly-silicon. For example, the etching rate for $SiO_2$ may range from approximately 50 angstroms per second (Å/s) to 56 Å/s and the etching rate for poly-silicon may range from approximately 5 Å/s to 8.5 Å/s. The selectivity ratio of $SiO_2$ to poly-silicon may therefore range from approximately 5.88 to 11. Accordingly, while portions of the second dielectric layer 26 which may include $SiO_2$ is completely etched, the electrical contact regions 24-2 that include poly-silicon may be slightly etched during the anisotropic etching process. The second vias 33 may thus expose the electrical contact regions 24-2.

Although in the present example the first vias 30 are formed before the second vias 33, however, a person skilled in this art should understand that the sequence of forming the first vias 30 and the second vias 33 may be interchangeable.

Figure 2H:
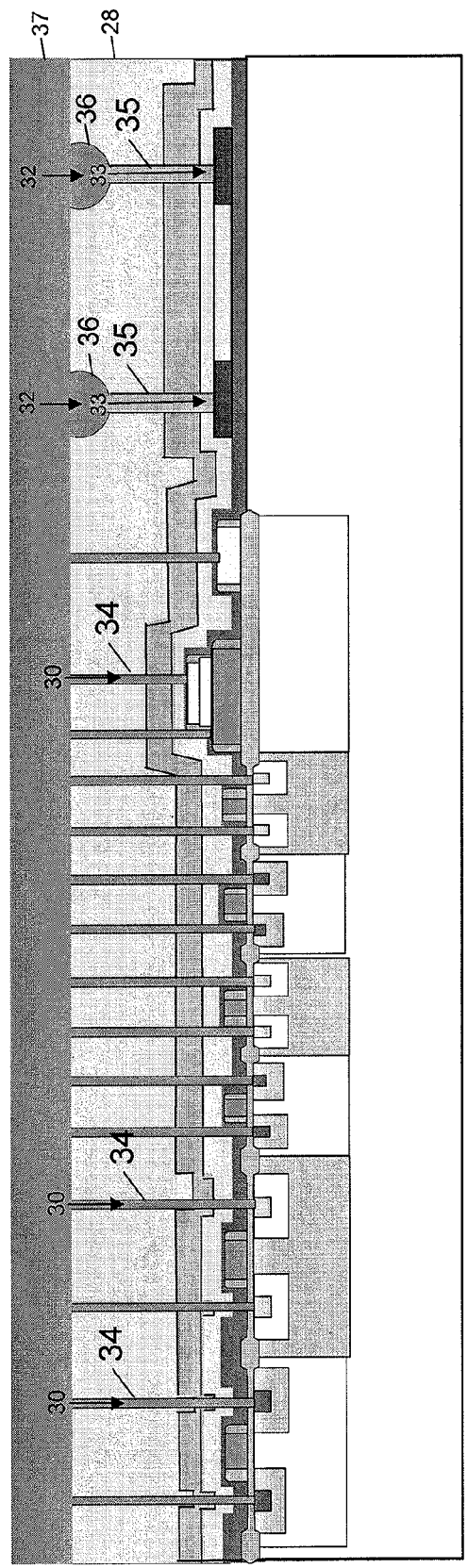

Referring to FIG. 2H, the patterned second mask layer 31 may then be removed and a second conductive layer 37 may be formed on the fourth dielectric layer 28 by, for example, a sputtering process. The second conductive layer 37 fills the first vias 30 and the second vias 33, resulting in first contacts 34 at the first region and second contacts 35 and pads 36 over the contact regions 24-2 at the second region of the substrate 20. In one example, the second conductive layer 37 may include an alloy of aluminum and copper (AlCu). Furthermore, the second conductive layer 37 may have a thickness of approximately 7000 Å.

Figure 2I:
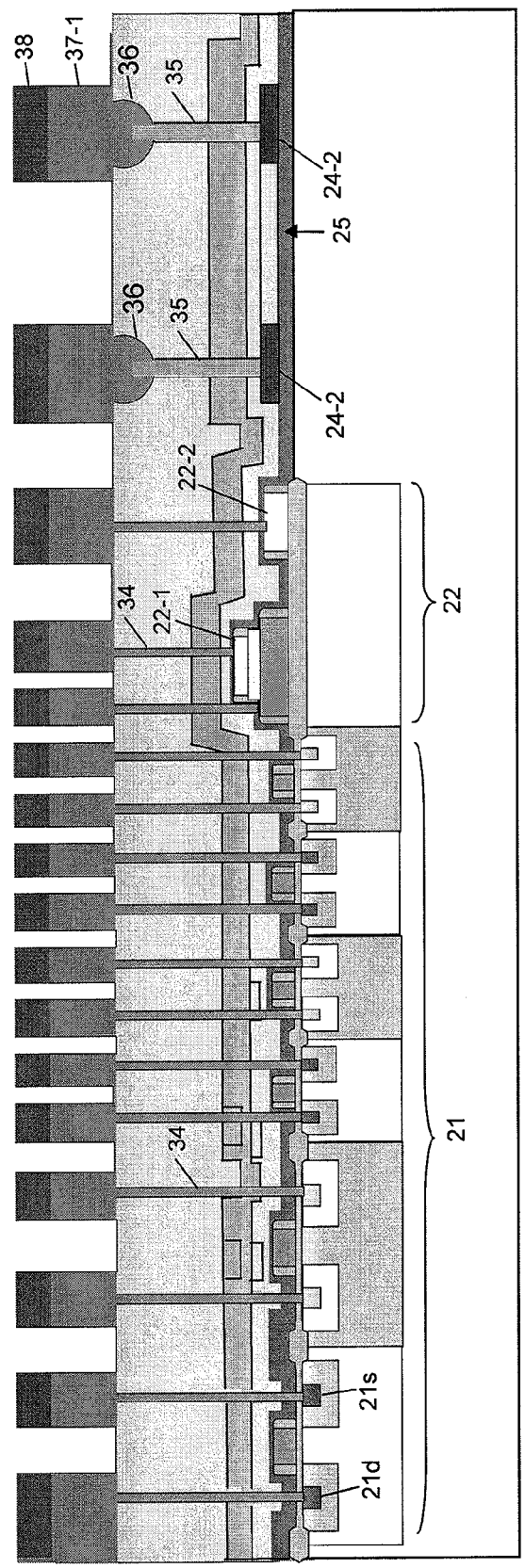

Referring to FIG. 2I, a patterned third mask layer 38 may be formed on the second conductive layer 37. Using the patterned third mask layer 38 as a mask, the second conductive layer 37 may be etched, resulting in a patterned second conductive layer 37-1. The patterned second conductive layer 37-1 may serve as an interconnection layer to electrically couple with the first contacts 34 and the pads 36. Specifically, through the interconnection layer, i.e. the patterned second conductive layer 37-1, the drain 21d and source 21s of each of the MOSFETs 21, the peripheral devices 22 and the electrical contact regions 24-2 of the sensing resistor may be electrically coupled to an external circuit.

Figure 2J:
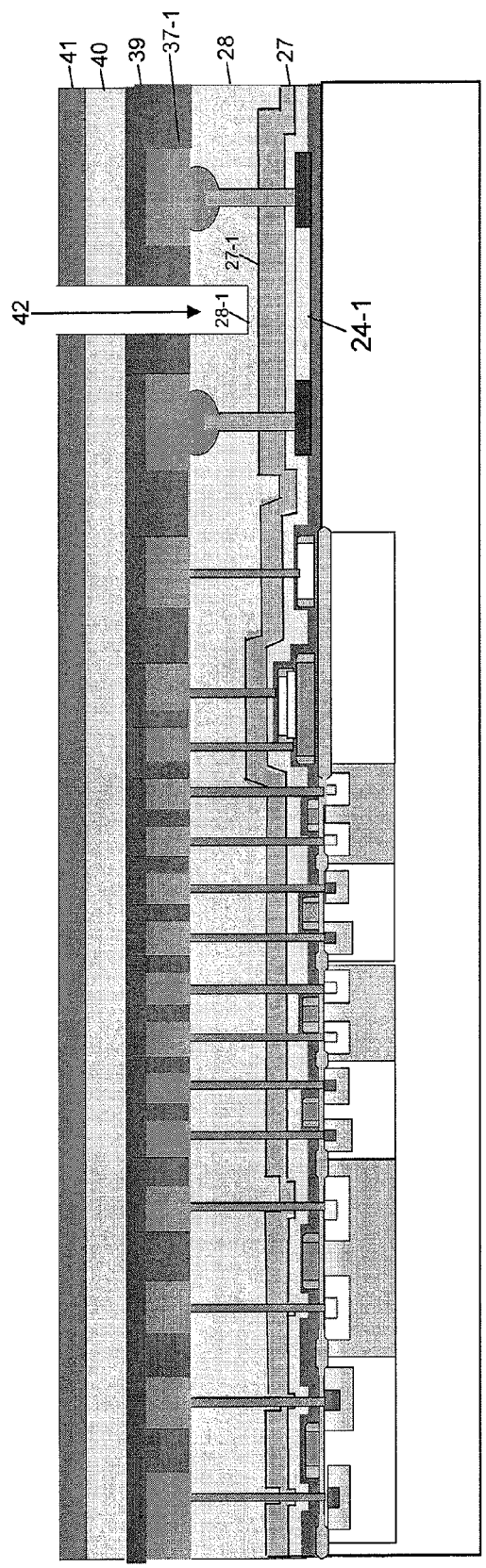

Referring to FIG. 2J, the patterned third mask layer 38 may then be removed and a fifth dielectric layer 39 may be formed on the fourth dielectric layer 28 and the patterned second conductive layer 37-1 by a deposition process. In one example, the fifth dielectric layer 39 may include $SiO_2$ having a thickness of approximately 2000 Å.

Furthermore, a sixth dielectric layer 40 may be formed on the fifth dielectric layer 39 by a deposition process. In one example, the sixth dielectric layer 40 may include $Si_3N_4$ having a thickness of approximately 7000 Å. The fifth and the sixth dielectric layers 39 and 40 may together serve as a passivation layer to provide electrical isolation for the patterned second conductive layer 37-1. In addition, with the rigidness of $Si_3N_4$, the sixth dielectric layer 40 may provide physical protection for the patterned second conductive layer 37-1 to avoid damage from subsequent processes.

Next, a patterned fourth mask layer 41 may then be formed on the sixth dielectric layer 40. Using the patterned fourth mask layer 41 as a mask, a first opening 42 may be formed through the fifth and sixth dielectric layers 39 and 40 into the fourth dielectric layer 28 by an anisotropic etching process. The first opening 42 may therefore expose a portion 28-1 of the fourth dielectric layer 28 over the first portion 24-1 of the first conductive layer 24. The exposed portion 28-1 may be at a distance ranging from approximately 1000 Å to 1500 Å from the upper surface 27-1 of the third dielectric layer 27.

Figure 2K:
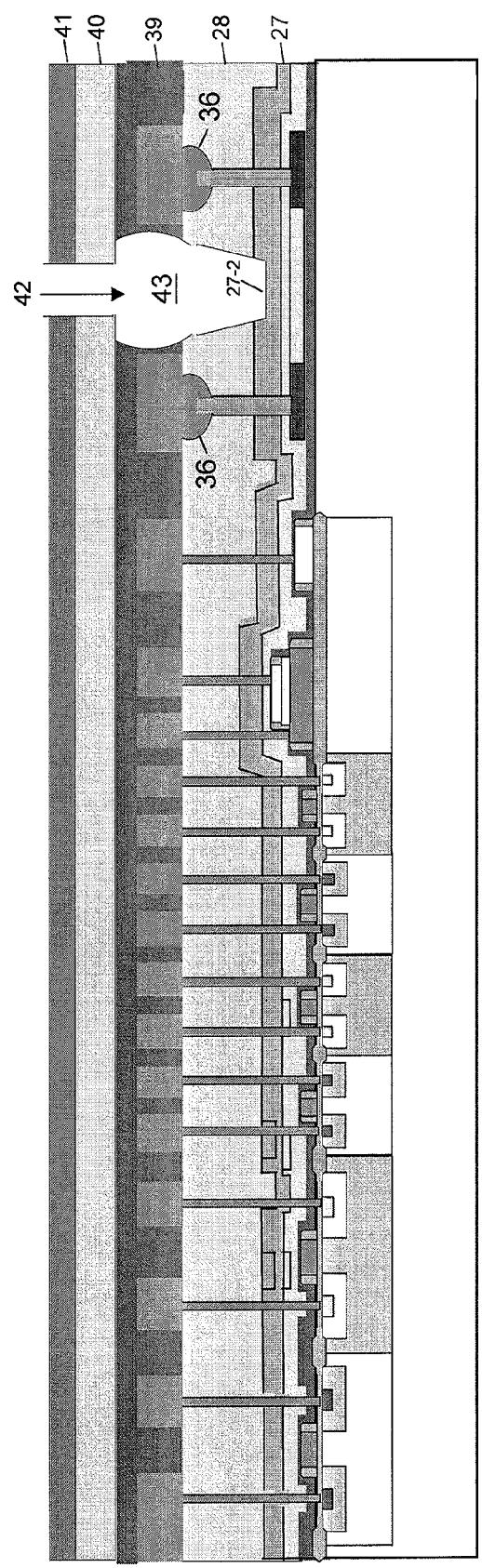

Referring to FIG. 2K, a chamber 43 between the pads 36 may be formed by etching the fourth and the fifth dielectric layers 28 and 39 from the first opening 42 by an isotropic etching process, using the patterned fourth mask layer 41 as a mask. Specifically, the isotropic etching process may have a higher etching-selectivity for $SiO_2$ than for $Si_3N_4$. For example, the etching rate for $SiO_2$ may range from approximately 11 Å/s to 12 Å/s and the etching rate for $Si_3N_4$ may range from approximately $1.05 \times 10^{-1}$ Å/s to $1.7 \times 10^{-1}$ Å/s. The selectivity ratio of $SiO_2$ to $Si_3N_4$ may therefore range from approximately 64.7 to 114. Accordingly, after the isotropic etching process, the fifth dielectric layer 39 that may include $SiO_2$ and the fourth dielectric layer 28 that may include USGOX and BPSG between the pads 36 may be largely etched while the sixth dielectric layer 40 that may include $Si_3N_4$ around the first opening 42 and the third dielectric layer 27 that may include $Si_3N_4$ under the first opening 42 may be slightly etched. The chamber 43 may serve as a channel region for the bio-sensor, which will be discussed in later paragraphs by reference to FIG. 3. In addition, after the above-mentioned isotropic etching process, the portion 28-1 of the fourth dielectric layer 28 may be totally etched while the third dielectric layer 27 under the first opening 42 may be slightly etched, that may in turn expose a portion 27-2 of the third dielectric layer 27 and leave the thin first and second insulators, i.e. the second and third dielectric layers 26 and 27 over the sensing resistor 25.

Figure 2L:
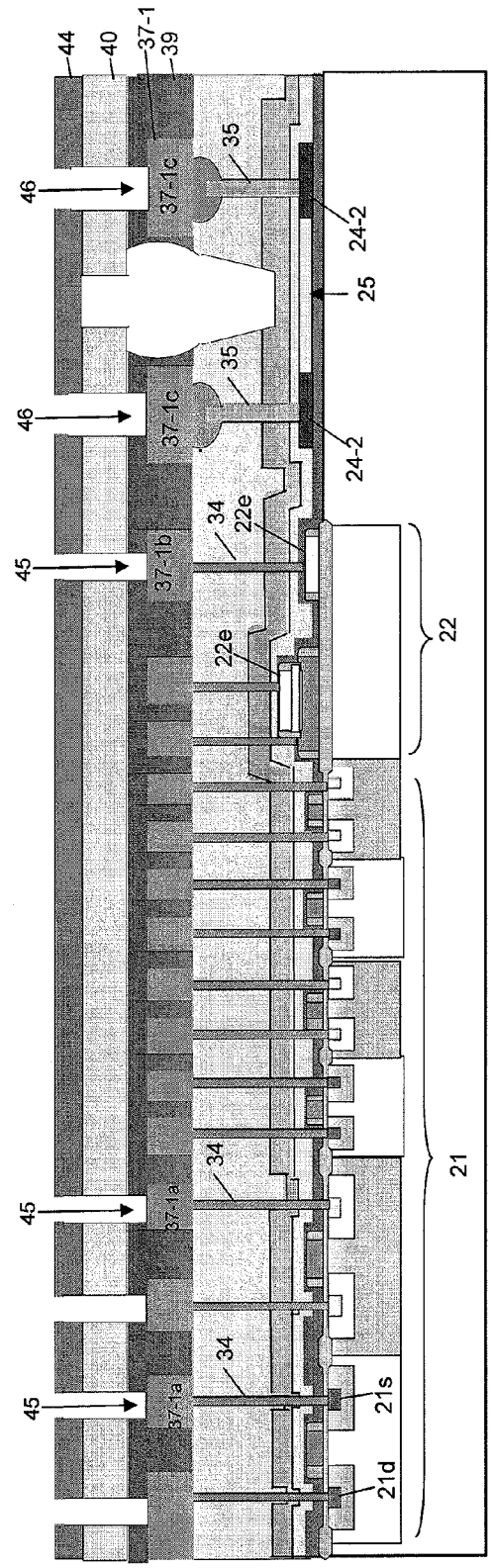

Referring to FIG. 2L, the patterned fourth mask layer 41 may then be removed and a patterned fifth mask layer 44 may be formed on the sixth dielectric layer 40. Using the patterned fifth mask layer 44 as a mask, second openings 45 and third openings 46 may be formed through the sixth dielectric layer 40 into the fifth dielectric layer 39 by a dry etching process. Specifically, the second openings 45 may substantially expose portions 37-1a of the patterned second conductive layer 37-1 over the first contacts 34 associated with the source and drain regions 21s and 21d of the MOSFETs 21. The exposed portions 37-1a may serve as pads for the MOSFETs devices 21, which may operate at operating voltages of 12V, 5V and 3V. Furthermore, the second openings 45 may substantially expose portions 37-1b of the patterned second conductive layer 37-1 over the first contacts 34 associated with the peripheral devices 22. Moreover, the third openings 46 may substantially expose portions 37-1c of the patterned second conductive layer 37-1 over the second contacts 35 associated with the electrical contact regions 24-2 of the sensing resistor. The exposed portions 37-1c may serve as pads for the sensing resistor of the bio-sensor.

Figure 2M:
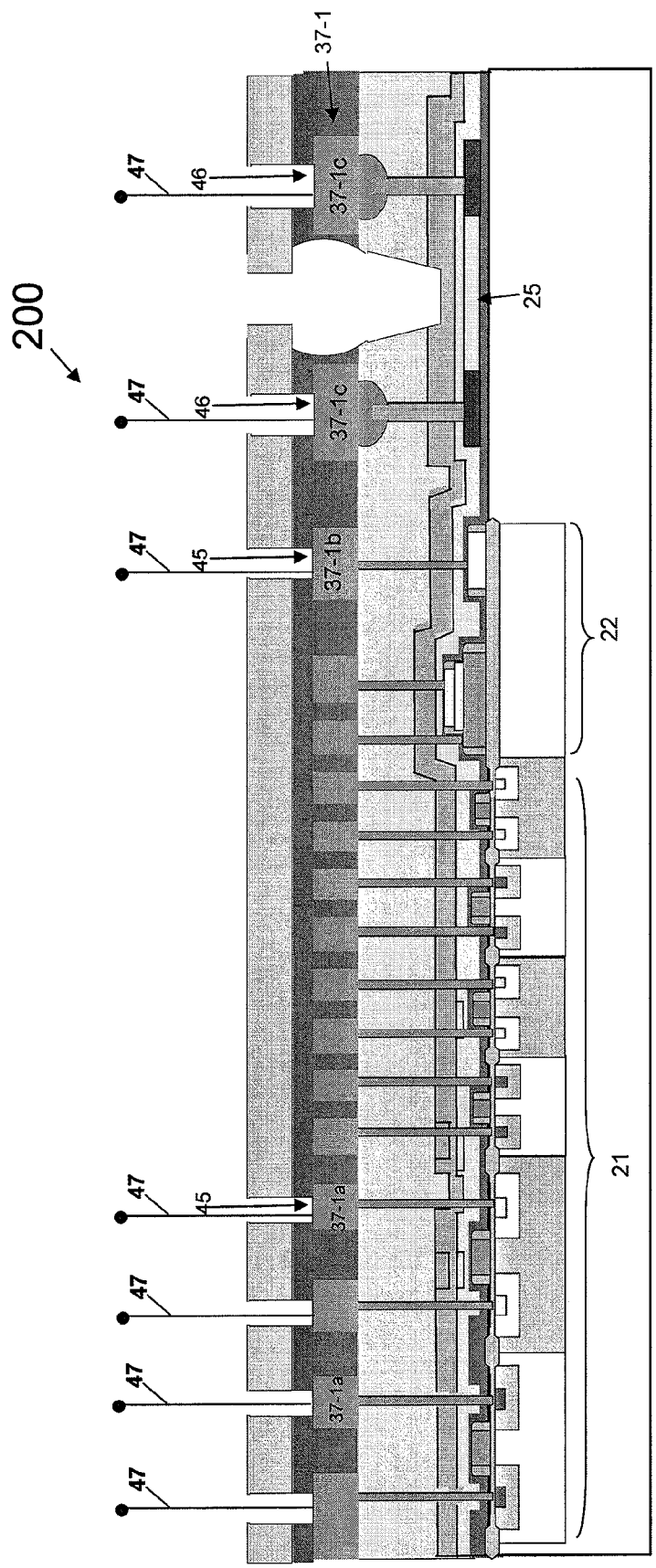

Referring to FIG. 2M, the patterned fifth mask layer 44 may then be removed and external connecting wires 47 may be coupled to the exposed portions 37-1a, 37-1b and 37-1c of the patterned second conductive layer 37-1. Through the connecting wires 47, a semiconductor device 200 including the CMOS devices 21, the peripheral devices 22 and the bio-sensor 25 may be configured to perform a dedicated or customized function.

Figure 3:
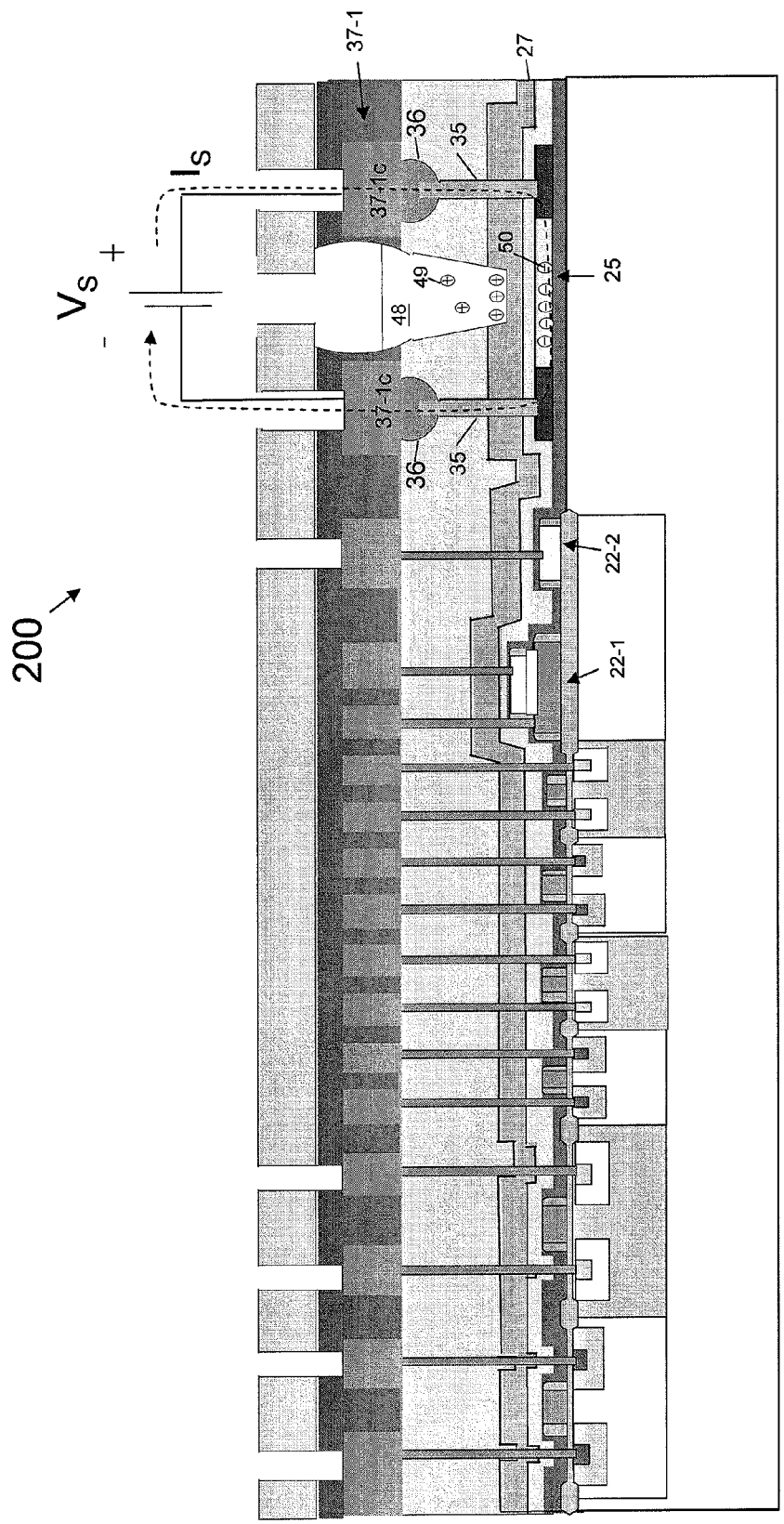
FIG. 3 is a schematic cross-sectional view illustrating an exemplary operation of the semiconductor bio-sensor illustrated in FIG. 2M.

FIG. 3 is a schematic cross-sectional view illustrating an exemplary operation of the semiconductor device 200 illustrated in FIG. 2M. Referring to FIG. 3, in operation, a voltage Vs may be applied to the sensing resistor 25, inducing a current Is that may flow through portions 37-1c of the patterned second conductive layer 37-1, pads 36, second contacts 35 and the sensing resistor 25 of the bio-sensor. The chamber 43, as the channel region for the bio-sensor, may receive electrolyte 48 sampled from a bio-organism under testing (not shown). The sensing resistor 25 may thereafter sense ions 49 in the electrolyte 48. Specifically, some of the ions 49 in the electrolyte 48 may contact the upper surface of the second insulator, i.e. the third dielectric layer 27. Through the relatively thin first and second insulators, i.e. the second and third dielectric layers 26 and 27, the ions 49 that contact the upper surface of the second insulator, i.e. the third dielectric layer 27 may further introduce ions 50 of an opposite polarity within the sensing-resistor 25. The introduced ions 50 within the sensing-resistor 25 may influence and therefore change the concentration of the lightly implanted impurity therein, that may in turn change the sheet resistance of the sensing resistor 25. Accordingly, the magnitude of the induced current Is flowing through the sensing resistor 25 may be changed given that the applied voltage Vs remains constant. Such change in the induced current Is may then be measured, and the ions 49 in the electrolyte 48 may be therefore sensed by the bio-sensor. Malfunction of the bio-organism under testing may lead to an abnormal concentration of ions 49, which may deviate from a standard value, introduce a deviated amount of ions 50 within the sensing resistor 25 and therefore cause a change in the resistance thereof. Hence, the malfunction of the bio-organism under testing may be detected by the bio-sensor. Furthermore, in the semiconductor device 200, the capacitor 22-1 may serve as a sound sensor, and the resistor 22-2 may serve as a thermopile sensor.

We claim:

1. A semiconductor bio-sensor comprising:
   a substrate;
   a first dielectric layer on the substrate;
   a patterned first conductive layer on the first dielectric layer, the patterned first conductive layer including a first portion and a pair of second portions to sandwich the first portion;
   a second dielectric layer on the patterned first conductive layer, the second dielectric layer having an etch rate greater than that of the patterned first conductive layer;
   a third dielectric layer on the second dielectric layer;
   a fourth dielectric layer on the third dielectric layer, the fourth dielectric layer having an etch rate greater than that of the third dielectric layer;
   a pair of pads over the second portions in electrical connection with the second portions;
   a patterned second conductive layer on the pads; and
   a channel region between the pads to expose the third dielectric layer.

2. The semiconductor bio-sensor of claim 1, wherein the first portion of the patterned first conductive layer includes a lightly doped impurity and the second portions include a heavily doped impurity.

3. The semiconductor bio-sensor of claim 1, wherein the second dielectric layer includes a material selected from one of silicon dioxide and silicon oxynitride.

4. The semiconductor bio-sensor of claim 1, wherein the third dielectric layer includes a material selected from one of silicon nitride and aluminum nitride.

5. The semiconductor bio-sensor of claim 1, wherein the fourth dielectric layer includes a first sub-layer of undoped silicon glass oxide (USGOX) and a second sub-layer of boron phosphate silicon glass (BPSG).

6. The semiconductor bio-sensor of claim 1 further comprising a passivation layer on the fourth dielectric layer to expose the channel region, wherein the passivation layer includes a fifth dielectric layer and a sixth dielectric layer on the fifth dielectric layer.

7. The semiconductor bio-sensor of claim 6, wherein the fifth dielectric layer includes silicon oxide and the sixth dielectric layer include silicon nitride.

* * * * *